United States Patent [19]
Cannon

[11] Patent Number: 5,860,739
[45] Date of Patent: Jan. 19, 1999

[54] AUTOMATIC MIXING SYRINGE FOR DENTAL MATERIALS

[76] Inventor: Mark L. Cannon, 548 Wayland Ave., Kenilworth, Ill. 60043

[21] Appl. No.: 811,202

[22] Filed: Mar. 5, 1997

[51] Int. Cl.[6] .................................................. B01F 15/04
[52] U.S. Cl. .................................. 366/177.1; 366/181.5; 366/189; 222/137
[58] Field of Search ............................ 366/177.1, 179.1, 366/181.1, 181.5, 189, 162.1, 158.5; 222/135, 137

[56] References Cited

U.S. PATENT DOCUMENTS

| | | | |
|---|---|---|---|
| 4,370,062 | 1/1983 | Moody | 366/181.5 |
| 4,538,920 | 9/1985 | Drake | 366/181.5 |
| 4,668,097 | 5/1987 | Nygren et al. | 366/177.1 |
| 4,913,553 | 4/1990 | Falco | 366/177.1 |
| 4,934,827 | 6/1990 | Taschke et al. | 366/177.1 |
| 5,211,311 | 5/1993 | Petcen | 366/177.1 |
| 5,242,115 | 9/1993 | Brown | 366/181.5 |

*Primary Examiner*—Tony G. Soohoo
*Attorney, Agent, or Firm*—Walter C. Ramm

[57] ABSTRACT

A dental syringe system including a gun element, for association with a tip element, to mix and dispense respective dental materials of and while the materials yet have plastic or flowable consistency. The gun has a chamber in which to load cartridges of respective such materials, a motor, two plungers, a ram to move relative to the gun, and a trigger-and-gears mechanism to operate the plungers in association with the motor, and separately to operate the ram. The trigger is mounted to move to and between several positions. At one such position, the trigger operates the motor to advance the plungers into respective sites where such cartridges may be loaded and, when cartridges are so loaded, to express materials from the cartridges and the gun. At a subsequent such position, the trigger extends the ram from the gun, and the motor and the plungers disengage. The tip element has a trans-tip passage with a cavity, vanes within the cavity, and a channel from the cavity. When the gun is so loaded and carries the tip element so that the chamber is in communication with the cavity, the trigger is operable in two respects: first, to advance the plungers and to express material from each cartridge into the cavity, and, second, to extend the ram into the cavity, to mix the materials on the vanes, and to urge mixed materials from the tip element via the channel. Two trigger-and-gear mechanisms for the gun are disclosed.

14 Claims, 2 Drawing Sheets

AUTOMATIC MIXING SYRINGE FOR DENTAL MATERIALS

FIELD OF THE INVENTION

This invention relates to a syringe system for mixing and dispensing dental materials and, in particular, to such a syringe system characterized by low wastage of the materials, better dispensing accuracy, and related advantages.

BACKGROUND OF THE INVENTION

Current mixing and dispensing practices for dental materials, such as those for restoration and cementation, involve notable waste of these usually expensive materials. Mixing and dispensing techniques often utilize substantially more of the materials than are actually required for a dental procedure. In many situations, an assistant dispenses the materials onto a mixing pad, such as a piece of wax paper, and mixes them by hand there. In these situations, the assistant rather crudely estimates needed amounts of materials, and sometimes mixes too much and sometimes too little. This technique has the further disadvantage of introducing gross amounts of ambient air into the materials, thus tending adversely to affect their physical properties.

Moreover, currently available syringes and similar implements for mixing and dispensing dental materials typically feature a tip into which gross amounts of dental materials are forced and convoluted. Thus, the implements have disadvantage in that they tend to involve and to deliver an overly large bolus of materials and, again, waste expensive materials.

SUMMARY OF THE INVENTION

In summary, the syringe system of this invention overcomes the disadvantages, as described, of hand-mixing dental materials as well as of earlier implements for mixing and dispensing such materials.

In this summary and elsewhere in this specification

"procedure" means a dental procedure, such as restoration or cementation.

"material" means a dental material having a generally flowable or plastic consistency and which, prior to use in or for purpose of a procedure, may be contained in and presented from a containment such as a conventional cartridge.

"materials" means two materials in a functionally combined or mixed status.

"unit" means, as well understood in the art, an amount of materials comprising one unit of the number of such units as needed or indicated for a procedure.

The general object of this invention is a syringe system for better practice of dentistry—to the benefit of dental practitioners and patients—and to overcome the imprecision, waste, and other disadvantages likely to attend hand mixing of materials and the unwanted structural and operational characteristics of earlier dental syringes. Within this general object, particular objects of the invention include, as to practitioners, assistants and patients, proper mixing of materials, prompt expulsion of unwanted air from a bolus of to-be-dispensed materials, better accuracy in amounts of materials dispensed, quick delivery of one or more units in terms of specific setting or curing times, convenience and ease of use, and improved cost and efficiency factors.

To achieve these objects, the syringe system has a gun-like member (the "gun") and may include a tip member (the "tip") for or on the gun. The gun has a chamber in which to load two cartridges of materials; an orifice from the chamber; a small electric motor; a shaft with a ram, and to be driven by and to disengage from the motor; two plungers; and, a trigger-and-gears mechanism whereof the trigger serves to operate the motor, the plungers and the ram.

The trigger has "off", partly-depressed, and fully-depressed positions. The shaft is adapted to move relative to the gun. With the trigger partly depressed, the motor is connected with a power source and advances the plungers into the sites. When the trigger is fully depressed, the shaft disengages from the motor, and forcefully extends the ram out from the gun by way of the orifice.

The tip has a trans-tip conduit with a cavity and a channel from the cavity, and, as on the gun, disposes the cavity to communicate with the chamber by way of the orifice. The tip also has internal vanes in the cavity to spatulate and to mix materials introduced to the cavity from outside the tip, and to collapse, under applied deflective force, to assure an open route for such materials from the cavity by way of the channel.

When the gun carries a tip and is loaded with cartridges of respective materials, and the trigger is at partly-depressed position, the motor in association with the trigger-and-gears mechanism serves slowly to advance the plungers to express materials from the cartridges and to feed them into the cavity, by way of the orifice, and to be mixed on the vanes. The feeding and mixing fills the cavity, and tends to entrap some air into the materials, and to force an air bubble from the tip via the channel. Then, when trigger is fully depressed, the ram extends through the orifice, and into the cavity and materials there, to apply deflective force on the vanes, further to expel entrapped air, and quickly to urge one or more units of mixed materials from the tip via the channel.

Typically, the gun is a hand-operable device characterized by compact size, light weight, and nicely responsive trigger action, and, in terms of measures to combat infection, is readily disinfected; and, the tip is a disposable member so, again having regard for anti-infective measures, a fresh tip may be provided for each patient. Thus, the syringe system is capable of easy, reliable, safe and effective use by practitioners and assistants to mix and dispense materials.

REFERENCE NUMERALS AND CHARACTERS

Figure 1:
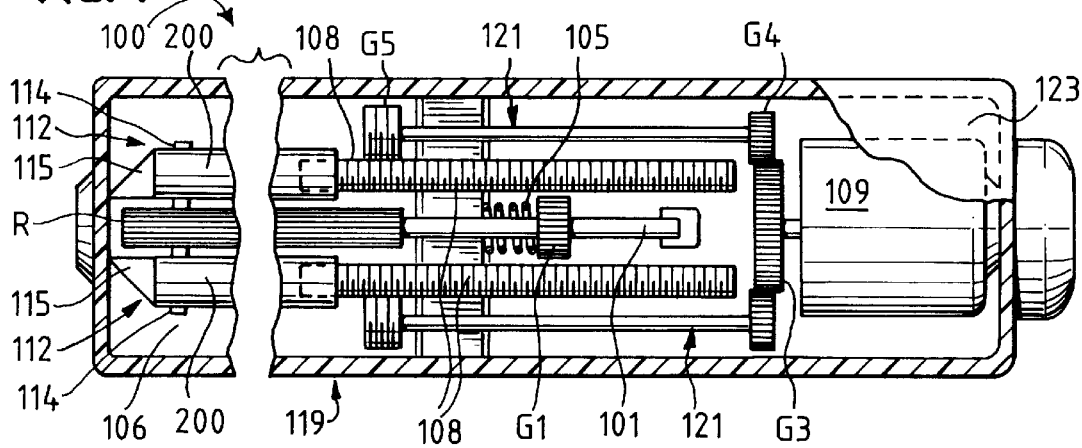
FIG. 1 is a plan view of an exemplary gun for a syringe for dental materials. Much of the gun's upper outer wall portion is removed to show internal parts and components, including parts of the trigger-and-gears mechanism.

In the drawings and in this specification these reference numerals and characters identify parts, elements, features, aspects and other matters of or with reference to the dental syringe system of this invention:

Numeral 100 is an exemplary gun of the syringe system. Of or with reference to gun 100

101 is a first shaft carrying gear G1 and defining ram R.

102 is the trigger pivotally carried on mounting M.

103 is an electrical contact point.

104 is the upper arm of trigger 102.

105 is a spring.

106 indicates the chamber.

107 indicates an orifice in the forward portion of gun 100.

108 is each of first and second plungers.

109 is an electric motor in a housing.

111 is a second shaft carrying gears G2 and G3.

112 indicates each of two loading sites in chamber 106.

114 is a clip at a site 112.

115 is a feeder assembly at a site 112.

116 is the pistol grip.

117 indicates interior space within grip 116.

118 is a battery in space 117.

119 is the barrel.

121 is each of two side assemblies each with a gear G4, a gear G5, and a shaft intermediate and serving to connect gears G4 and G5.

122 is an interior wall portion.

123 is exterior wall portions.

Numeral 200 is a cartridge of material. Of or with reference to a cartridge 200

201 is the delivery end.

202 is the plug end.

Numeral 300 is a tip for gun 100. Of and with reference to tip 300

301 is wall portions.

302 indicates a trans-tip conduit or interior passage.

303 indicates the cavity.

304 indicates the channel.

305 is one of several collapsible vanes in cavity 303.

Numeral 400 is an alternate trigger-and-gears mechanism for a gun, such as gun 100, of this invention. In or with reference to mechanism 400

101' is a first shaft carrying gear G6, and defining ram R' at one end.

102' is the trigger as pivotally mounted on mounting M'.

104' is the upper arm of trigger 102'.

105' is a first spring.

108' is each of first and second plungers.

109' is an electric motor in a housing.

121' is each of two side assemblies each with a gear G4', a gear G5' and a shaft intermediate and connecting gears G4' and G5'.

122' is in interior wall portion of a gun of which mechanism 400 is a part.

401 is a second shaft carrying gear G7 and gear G8.

402 indicates a bearing for shaft 401.

403 is an alignment rod.

404 is a second spring.

F is a small button or flange at the other end of shaft 101'.

G9 is a pinion gear on the shaft of motor 109'

G10 is an orbital gear.

DETAILED DESCRIPTION OF THE INVENTION

Embodiments and methods of this invention, in their several aspects and elements, including structure and operability, and according to this description, are best modes and preferred embodiments of the invention. In some such aspects and elements, the invention may be an improvement of devices or of methods otherwise known to the art.

Preliminarily, cartridges 200 are articles of commerce or may be specially fabricated for the syringe system of this invention. Typically, a cartridge comprises a tubular containment, and has ends 201 and 202. End 202 is adapted to receive a plunger to enter and substantially to occupy the cross-sectional area of and, as to be described, to express a material from the containment. End 201 is adapted to open and so to provide delivery of a material under influence of a plunger at end 202.

Figure 2:
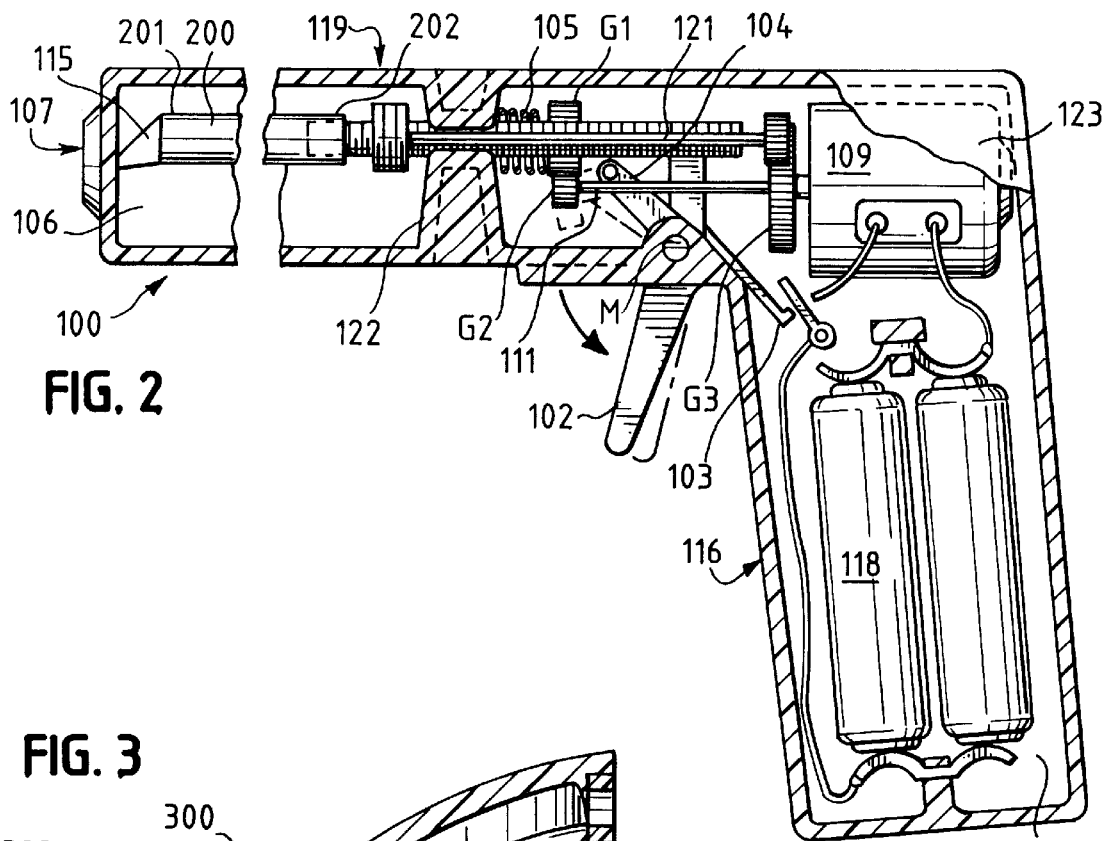
FIG. 2 is a side elevation view of the gun. Again, much of the outer wall portion is removed to show the interior.

A syringe comprising gun 100, and to carry a tip 300, is provided to mix and then deliver auto-curing or dual curing materials such as materials for dental restoration or cementation. FIGS. 1–2 show structure and motive elements of an exemplary embodiment of the gun. As to structure, the gun has walls 123, which define grip 116 and barrel 119, and trigger 102, which is on and pivotal of mounting M. The trigger has arm 104, and may be moved on mounting M to and between each of three positions: "off" or first, partly-depressed or second, and fully-depressed or third. Arm 104 and shaft 101 are pivotally linked. Chamber 106 is in the forward part of the barrel, orifice 107 is at the forward end of the barrel, and first and second sites 112—each for loading a cartridge 200—are in a parallel arrangement in the chamber. Each site 112 may include a clip 114 to hold a loaded cartridge and a feeder 115 to receive end 201 of the cartridge, and to conduct material from the cartridge to or through the orifice. Feeders 115 taper from larger to smaller cross section, and may be integral of and conventionally formed with barrel 119. Access to the chamber, for manual loading of cartridges or other purposes, may be through an open top of the chamber.

Continuing to refer to FIG. 1–2, and as to motive elements, gun 100 carries motor 109 and shaft 111, which extends from, is adapted to be rotated by, and is flexible—that is, extensile as to—the motor. Typically, the motor is a small electric motor, and, as shown, is adapted to connect with a power source such as battery 118 in space 117. Shaft 101 carries gear G1. Shaft 111 carries gears G3 and G2, with the former proximal and the latter distal as to the motor, so they are spaced from each other. The gun also carries shaft 101 in association with arm 104, first and second plungers 108, and first and second assemblies 121. Typically, the plungers are elongate, cylindric and parallel. The first plunger is aligned with the first site, and the second plunger is aligned with the second site. The first plunger and first side assembly are associated with each other and may be described as right-side components. The second plunger and the second side assembly are associated with each other and may be described as left-side components. Further, as shown: gears G1–G4 are spur gears, gears G5 are worm gears and each plunger is threaded or otherwise adapted to be driven by a gear G5, and, when so driven, to track toward and into the site with which it is aligned. Shaft 101 includes ram R, and is arranged to pass through and to be supported in an opening in wall portion 122. The trigger, shafts 101 and 111, the side assemblies, and gears G1–G5 may be described as an exemplary trigger-and-gears ("t&g") mechanism.

Trigger 102 controls characteristic kinematics of gun 100. Spring 105—shown as an helical spring—is operative between wall 122 and a face of gear G1 to urge gears G! and G2 and gears G3 and G4, respectively, toward engaged status, and to bias the trigger to first postion. When the trigger is at first position the gun is inoperable, motor 109 is disconnected from battery 118, gear G3 is in at least partial engagement with gears G4, gears G1 and G2 are in at least partial engagement with each other, one gear G5 is engaged with each respective plunger 108, and ram R is in retracted position within chamber 106. When the trigger is partially depressed to second position—which entails only small displacement (see the short travel of contact 103)—battery 118 delivers power to the motor through contact 103, and to rotate shaft 111 and gears G2 and G3; gear G3 and gears G4 continue in engagement, and gears G4, as rotating on shaft 111, rotate the shafts of the side assemblies to drive gears G5 and so relatively slowly to advance each plunger toward and to track into the site 112 with which it is aligned. In terms of the relative size of the gun and the small amount of materials to comprise a unit, a retaively slow rate of advance of the plungers has no adverse effect. Where, as shown, gears G4 are identical, and gears G5 are of equal size and otherwise correspond, the plungers advance simultaneously and at the same rate. Other specific gearing arrangements could enable, if desired, different rates or ratio of advance in respect of the plungers.

As trigger 102 is fully depressed to third position, arm 104 describes forward angular movement on and as to mount M, and this angular movement translates to linear movement to extend shaft 111 forwardly, to disengage gear G3 from gears G4, and so to stop the advance of plungers 108; and, shaft 101 displaces forwardly to disengage gear G1 from gear G2, and directly, forcibly and quickly to project ram R, by way of orifice 107 and out of from and to extended position as to the gun.

Figure 3:
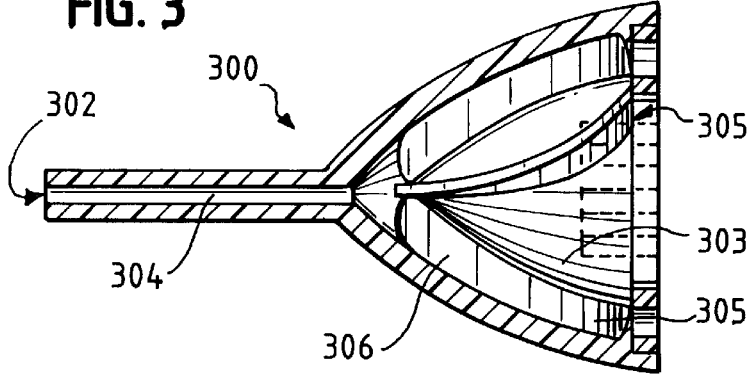
FIG. 3 is a side elevation view of a tip for the gun of FIGS. 1–2. A portion of the tip is removed to show internal features including the trans-tip passage.
Figure 4:
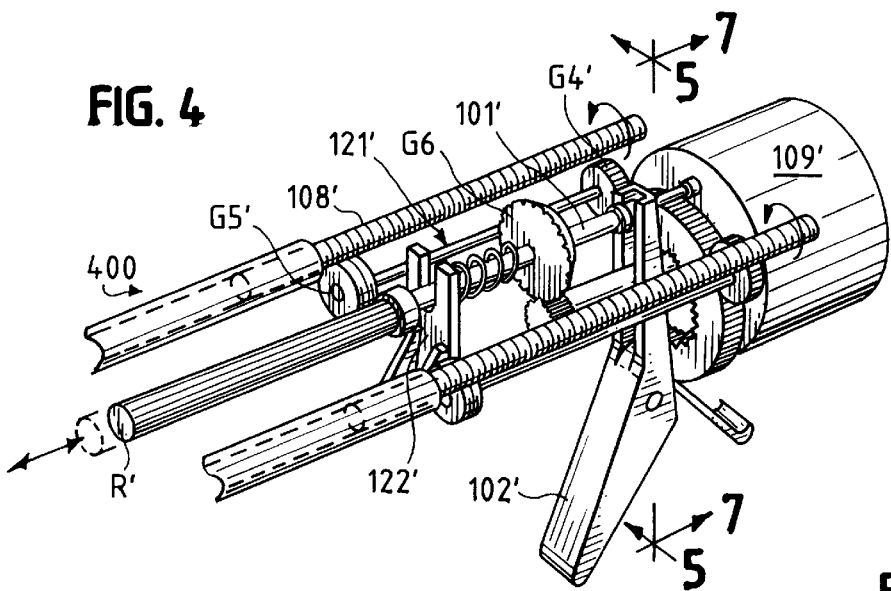
FIG. 4 is a perspective sketch of an alternate trigger-and-gears mechanism for a gun such as the gun of FIGS. 1–2. This alternate mechanism has two bevel gears.

FIG. 3 illustrates exemplary tip 300. This tip has wall portions 301 which define passage 302, with cavity 303 at one end of the passage, and channel 304 from the cavity and toward the other end of the passage. Vanes 305 are on the wall portions and in the cavity, and are adapted to collapse— that is, to displace or deflect toward the wall portions— under applied deflective force and so to afford better access to the channel. The tip is conventionally adapted for mounting on and demounting from gun 100 so, when mounted, it covers orifice 107, and the cavity is in communication with chamber 106 by way of the orifice.

An exemplary syringe comprises gun 100, and with a tip 300 mounted on the gun, as described. The syringe, as ready for service, two cartridges 200, each of a different material, loaded at respective sites 112 (see FIG. 1). Preferably, a loaded cartridge is held by clip 114 to be substantially coaxial with the plunger 108 which is aligned with the site, and has end 201 in feeder 115 and end 202 facing the plunger. When trigger 102 is at second position, the plungers advance to express materials from the cartridges via the feeders and the orifice into cavity 303, substantially to dispose a bolus of expressed materials in the cavity, to mix or spatulate the bolus on the vanes, and to expel, via channel 304, one or more bubbles of air that had been entrapped in the bolus. Appearance of the bubbles or the initial trace of expressed materials at the down-passage end of the channel may well signal that the materials of the bolus are ready for dispensing, and to shift the trigger to third position.

Then, when triggger 102 is moved to third position, as described, dispensing action promptly ensues. Ram R is extended into cavity 303 and into the bolus there, to exert force on the materials and apply deflective force on vanes 305, to cause the vanes to collapse and displace, and to dispense units from the syringe via channel 304.

FIGS. 4–7 illustrate mechanism 400 as an alternative t&g mechanism for a gun of this invention. In FIGS. 4–7, a prime on a reference numeral indicates a component which closely corresponds structurally and operationally to a component identified by the same numeral in FIGS. 1–2.

Mechanism 400 resembles but differs in several structural features from, the t&g mechanism of FIGS. 1–2; in this connection, these features of the mechanism 400 are notable: Rod 403 extends between the housing of motor 109' and shaft 101', and internally of shaft 101', to assure or reenforce alignment of shaft 101' in its movement, especially when ram R' moves to extended position. Arm 104' has a slotted, forwardly disposed groove to enable shaft 401 and rod 403 to pass through the arm in and in aid of their respective functions, and to retain button F. There is no positive linkage between arm 104' and shaft 101'; however, button F assures that the arm bears suitably on shaft 101' when trigger 102' moves to third position; further, spring 105' is operative between wall 122' and gear G6 to urge the arm toward first position of trigger 102' and to urge shaft 101' to fully retracted position corresponding to the the first position of the trigger. Shaft 401 is supported on and rotates in fixed position as to bearing 402, and unlike shaft 111, need not be extensile. Gears G6 and G7 are bevel gears whereof the respective axes of rotation are angularly displaced from each other by approximately a right angle.

Figure 7:
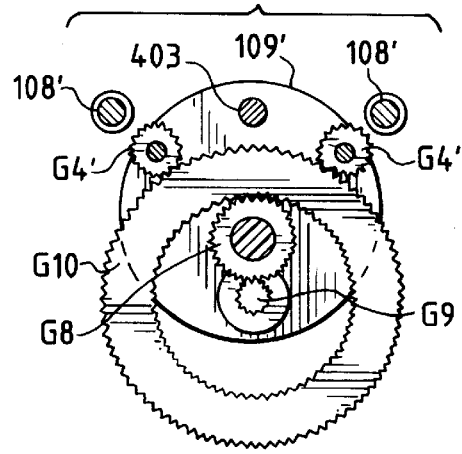
FIG. 7 is a sectional elevation view, along line 7—7 of FIG. 4, including five spur gears of a gear train of the FIG. 4 mechanism.

In mechanism 400, the gears may be further identified as follows: gear 6, a first gear; gear 7, a second gear; gear 8, a third gear, gears 4' fourth gears, gears 5', fifth gears; gear 9, a sixth gear and gear 10, a seventh gear. Gear G7 is adapted to drive gear G6 when they engage and trigger 102' operates the motor in housing 109' to rotate gear G9 and shaft 401 and so to drive gear G8. Gear G10 is orbital of gear G8 and intermediate of and operative between gears G8 and gears G4'. So operation of the motor is implemented by the gear train of gears G9, G8, G10, G4' and G5', and advances plungers 108'. FIG. 7 illustrates each G9–G4' portion of the train.

Figure 6:
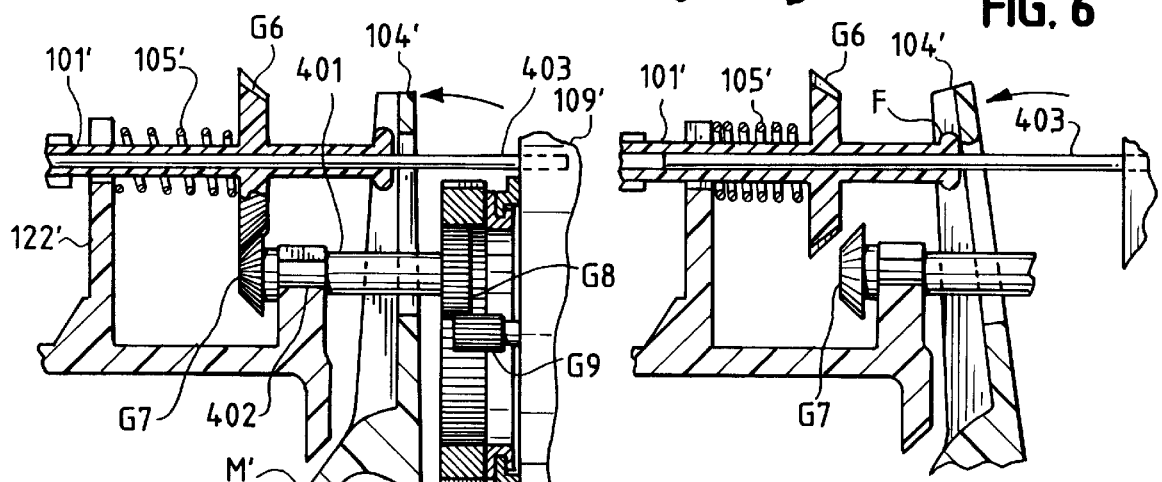
FIG. 6 is a fragment of the FIG. 5 view but with the bevel gears disengaged.
Figure 5:
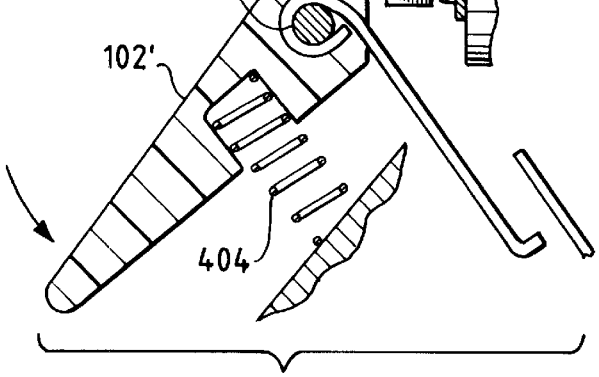
FIG. 5 is a sectional view, on line 5—5 of FIG. 4, of some elements of the FIG. 4 mechanism. The two bevel gears are engaged with each other.

As to further operational details of mechanism 400, FIG. 5 shows trigger 102' in first position, and FIG. 6, the trigger in third position. That is, as the trigger is depressed from second to third position, arm 104' rotates to bear upon and forwardly to displace shaft 101', against the resistance of spring 105', and so gear G6 likewise moves or displaces forwardly, and disengages from gear G7. Spring 404 normally biases the trigger to first position.

In addition to the exemplary gun, tip and t&g mechanisms disclosed in this specification, other embodiments and versions of a dental syringe system are within the spirit and scope of this invention.

What is claimed is:

1. A syringe member for association with a tip to be carried on the syringe member, the tip having an interior passage with a cavity and a channel from the cavity, for dispensing dental materials, and comprising a gun providing a chamber, an orifice and sites in the chamber for loading a respective cartridge of dental material at each site; and, adapted to carry such tip with the chamber in communication with the cavity via the orifice;

a motor on the gun;

a shaft carried within the gun, comprising a ram, and arranged for movement as to the gun, to be driven by the motor, and to disengage from the motor;

first and second plungers on the gun, and arranged to advance into respective ones of the sites when the motor drives the shaft; and, a trigger on the gun; linked with the shaft; arranged to be moved to and between each of first, second and third positions; and, adapted at the second position to connect the motor with a power source and so to operate the motor to drive the shaft, and, at the third position, to disengage the shaft from the motor;

so, when the gun is loaded with a cartridge of dental material at each site and carries such tip with the chamber in communication with the cavity via the orifice, the trigger at the second position serves to advance each one of the plungers into a respective one of the cartridges and to express materials from the cartridges, via the orifice, into the passage; and, movement of the trigger to the third position serves to disengage the shaft from the motor and to extend the ram, via the orifice, into the cavity to urge expressed materials from the tip via the channel.

2. The syringe member of claim 1 where each site includes a clip in the chamber to hold a cartridge and a feeder tube on the gun in which to place an end of the cartridge held by the clip of the site and by which to conduct dental material, as expressed from a cartridge at the site, from the gun via the orifice; and, the trigger is normally biased to the first position.

3. The syringe member of claim 2 where the gun has a pistol grip defining a space for a battery as the power source for the motor, the clip at each site is a spring clip, the plungers are in generally parallel arrangement and adapted simultaneously to advance, and the trigger is normally biased to the first position by spring means on the gun, and is pivotally linked with the shaft so that movement of the trigger from the third position to another one of the positions retracts the shaft into the gun.

4. The syringe member of claim 3 where the gun receives and carries, in the interior space defined by the pistol grip, a battery as the power source for the motor.

5. The syringe member of claim 1 where the shaft comprising a ram is a first shaft of the gun; the trigger is normally biased to the first position by spring means on the gun; and, the gun has a second shaft on and extending from the motor; a first gear on the second shaft and a second gear on the first shaft which are adapted to engage for driving the first shaft when the trigger is at the second position, and to disengage when the trigger is at the third position; and, a third gear on the second shaft arranged to drive the plunger when the trigger is at the second position, and to disengage as to the plungers when the trigger is at the third position.

6. The syringe member of claim 5 where the gun comprises a pistol grip defining an interior space for receiving a battery as the power source for the motor; each of the first, second and third gears is a spur gear; the second shaft is extensile so as to define increased length when the trigger is moved to the third position; and, the plungers are in generally parallel arrangement and adapted simultaneously to advance.

7. The syringe member of claim 5 where the gun comprises a pistol grip defining an interior space for receiving a battery to be the power source for the motor, each of the first and second gears is a bevel gear, the respective axes of rotation of the first and second gears are angularly displaced as to each other, and the first gear is adapted to drive the second gear.

8. A syringe, for dispensing dental materials in mixed status comprising a gun having a chamber, an orifice, and sites in the chamber for loading cartridges of respective dental materials;

an electric motor on the gun;

a shaft carried within the gun, defining a ram, and arranged to move as to the gun, and to be driven by and to disengage from the motor;

first and second plungers on the gun whereof each is implemented to advance into a respective one of the sites when the shaft is driven by the motor;

a trigger on the gun and arranged to be moved to and between each of first, second and third positions; linked to the shaft; adapted, at second position, to connect the motor with a power source and so to operate the motor to drive the shaft, and, at third position, to disengage the shaft from the motor; and, a tip with wall portions defining an interior trans-tip passage including a cavity and a channel from the cavity, with spatular vanes in the cavity and to be mounted on the gun with the cavity in communication with the chamber via the orifice, and whereof the vanes are adapted to displace toward wall portions defining the cavity under applied deflective force;

so when the gun is loaded with a cartridge of dental material at each site, and the tip is mounted on the gun, the trigger at second position drives the shaft to advance each one of the plungers into a respective one of the cartridges and to express dental materials from the cartridges, via the orifice, into the cavity and to mix expressed materials on the vanes; and, subsequent movement of the trigger to third position extends the ram, via the orifice and into the cavity and mixed materials there to apply deflective force to the vanes and to urge mixed materials from the tip via the channel.

9. The syringe of claim 8 where each site includes a clip in the chamber to hold a cartridge and a feeder tube on the gun in which to place an end of the cartridge held by the clip of the site and by which to conduct dental material, as expressed from a cartridge at the site from the gun via the orifice and into the cavity of the tip; and, the trigger is normally biased to the first position.

10. The syringe of claim 9 where the gun has a pistol grip defining space for a battery as the power source for the motor, the clip at each site is a spring clip, the plungers are in generally parallel arrangement and adapted simultaneously to advance, and the trigger is normally biased to first position by spring means operative between the trigger and the gun, and is linked to the shaft.

11. The syringe of claim 10 where the gun receives and carries, in the interior space of the pistol grip, a battery as the power source for the motor.

12. The syringe of claim 8 where the shaft comprising a ram is a first shaft of the gun, the trigger is normally biased to first position by spring means on the gun, and the gun includes a second shaft and a trigger-and-gears mechanism operative, in association with the motor, for advancing the plungers when the trigger is at second position.

13. The syringe of claim 12 where the trigger-and-gears mechanism comprises a first gear on the second shaft and a second gear on the first shaft, the first and second gears are bevel gears which are in engagement with each other when the trigger is at second position, and whereof the second gear displaces from engagement when the trigger is at third position.

14. The syringe of claim 13 where the axes of rotation of the first gear and the second gear are angularly displaced from each other, the trigger-and-gear mechanism includes a third gear on the second shaft and spaced from the first gear, and comprises a gear train including the third gear, two fourth gears, two fifth gears, a sixth gear, and a seventh gear, and whereof the sixth gear is a pinion gear on the motor and arranged to drive the third gear; the seventh gear is orbital of the third gear, intermediate the third gear and the fourth gears, and arranged to drive the fourth gears when the seventh gear is driven by the third gear, and each firth gear is arranged to advance one of the plungers when such fifth gear is driven by a fourth gear when the seventh gear is driven by the third gear and drives the fourth gears; each of the third, fourth and sixth gears is a spur gear; and, each of the fifth gears is a worm gear.

* * * * *